United States Patent
Durgin

[11] Patent Number: 6,050,995
[45] Date of Patent: Apr. 18, 2000

[54] POLYPECTOMY SNARE WITH MULTIPLE BIPOLAR ELECTRODES

[75] Inventor: Russ Durgin, Attleboro, Mass.

[73] Assignee: Scimed Lifesystems, Inc., Maple Grove, Minn.

[21] Appl. No.: 09/160,216

[22] Filed: Sep. 24, 1998

[51] Int. Cl.[7] .................................................. A61B 18/14
[52] U.S. Cl. ................................ 606/47; 606/48; 606/50
[58] Field of Search ................................ 606/41, 47, 48, 606/50

[56] References Cited

U.S. PATENT DOCUMENTS

| | | |
|---|---|---|
| 3,901,242 | 8/1975 | Storz .......................................... 606/48 |
| 4,311,143 | 1/1982 | Komiya . |
| 4,493,320 | 1/1985 | Treat . |
| 4,905,691 | 3/1990 | Rydell . |
| 4,976,711 | 12/1990 | Parins et al. ................................ 606/48 |
| 5,415,656 | 5/1995 | Tihon et al. . |
| 5,545,193 | 8/1996 | Fleischman et al. ....................... 606/41 |

*Primary Examiner*—Lee Cohen
*Attorney, Agent, or Firm*—Kenyon & Kenyon

[57] ABSTRACT

A device for cutting tissue from a body comprises a cutting member including a cable formed of first and second conductors insulated from one another. The first and second conductors are arranged in an alternating distribution along the cutting member with the first conductor having a plurality of exposed portions forming a plurality of first electrodes and the second conductor having a plurality of exposed portions forming a plurality of second electrodes. The first and second electrodes are distributed along a cutting edge of the cutting member.

13 Claims, 4 Drawing Sheets

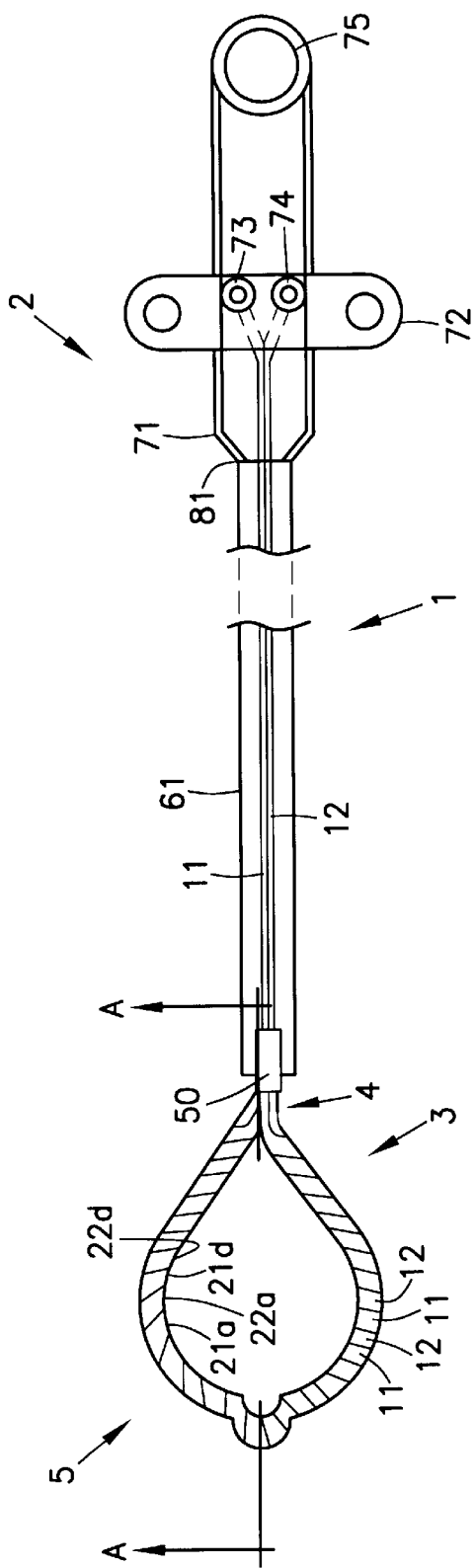
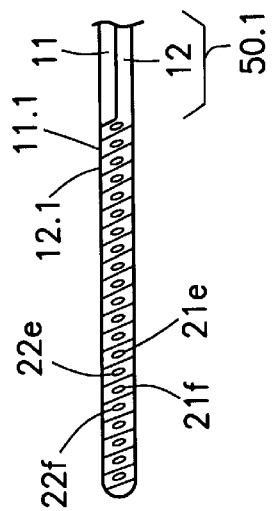
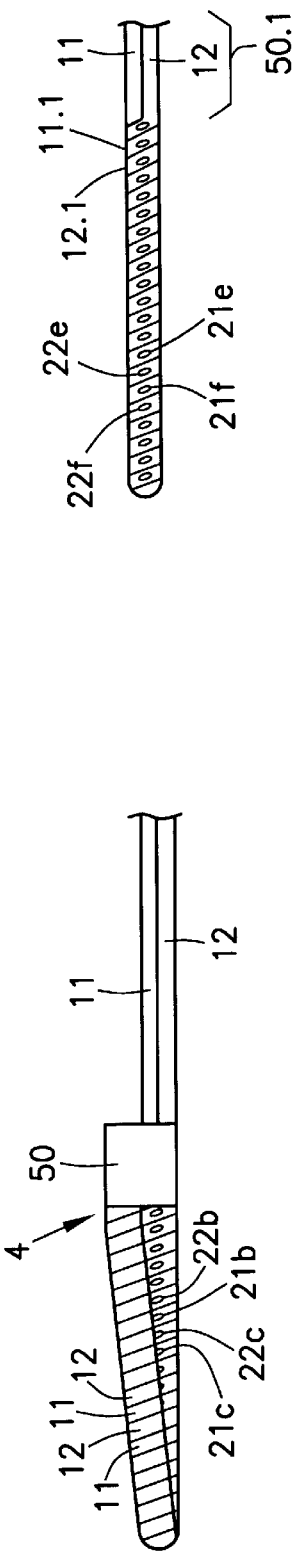

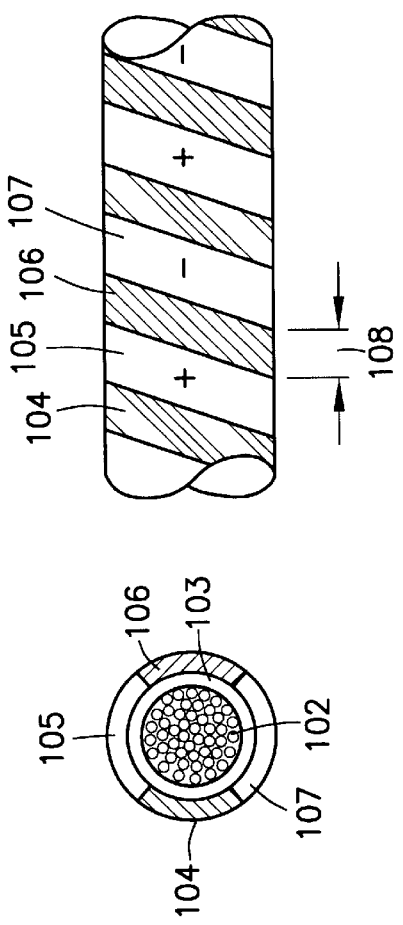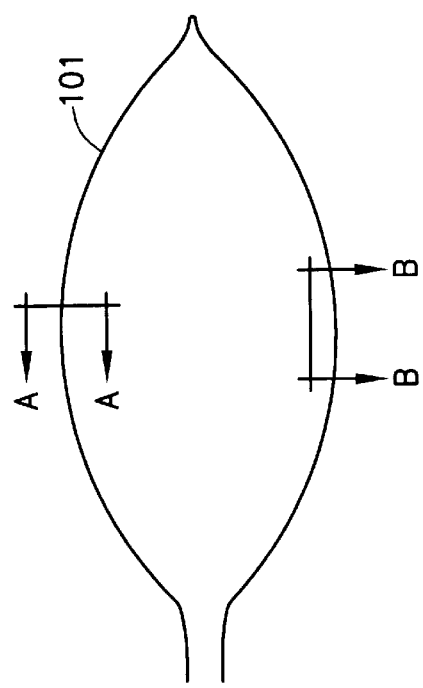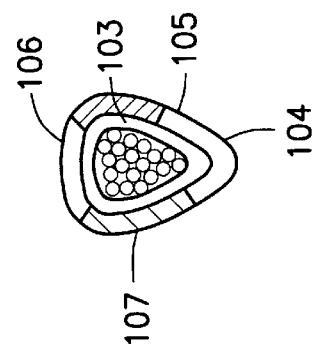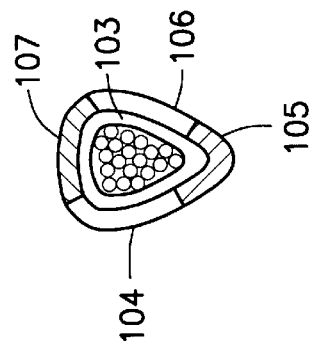

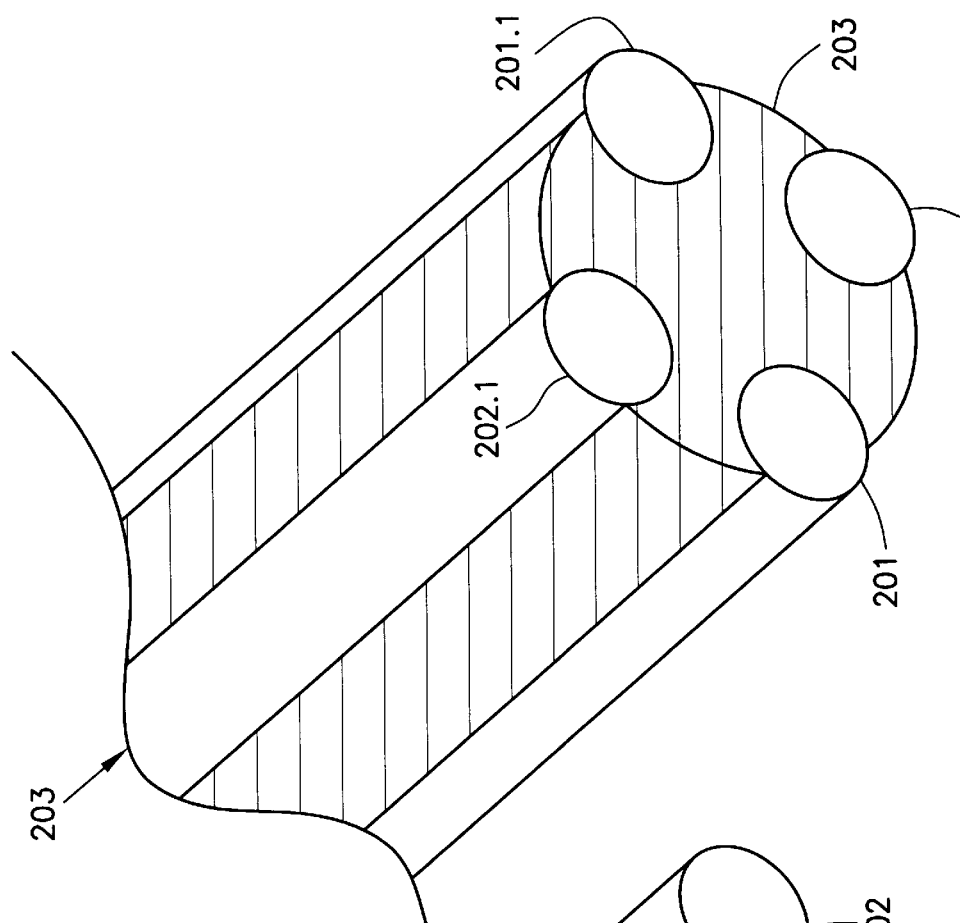
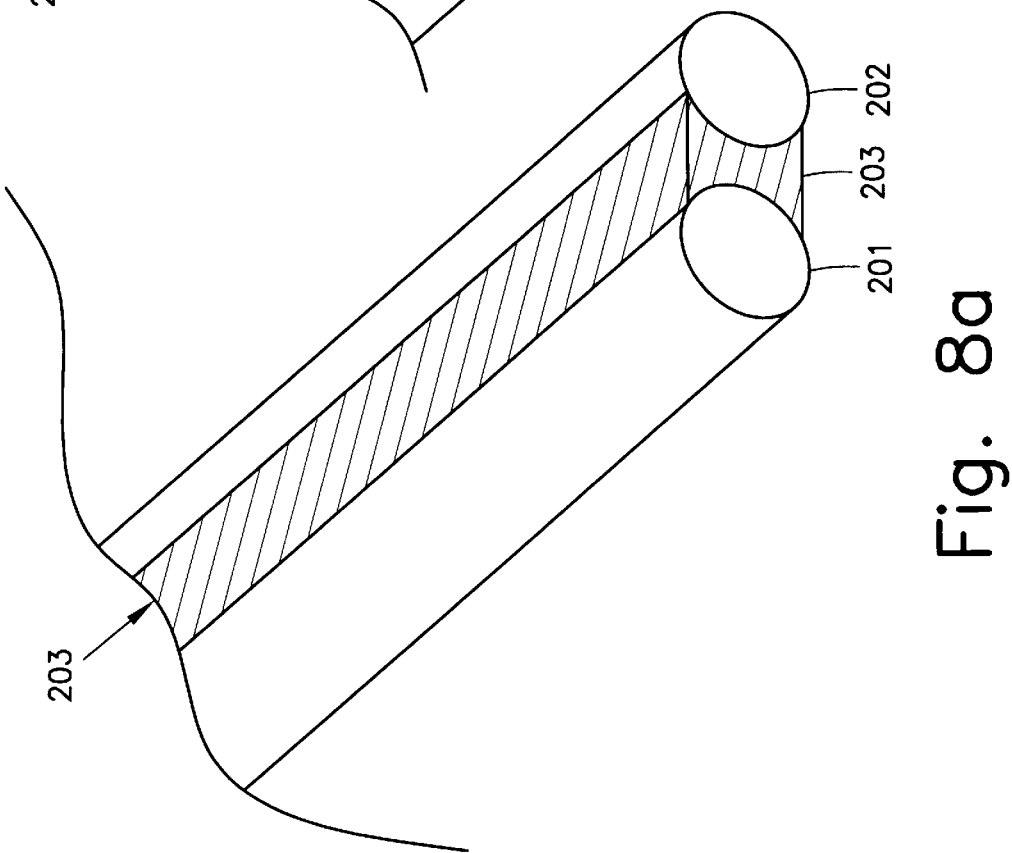

POLYPECTOMY SNARE WITH MULTIPLE BIPOLAR ELECTRODES

FIELD OF THE INVENTION

The present invention relates to electrosurgical devices, more particularly to electrosurgical devices having bipolar electrodes and most particularly relates to a bipolar polypectomy snare.

BACKGROUND INFORMATION

Monopolar tissue cutting devices such as snares are known which employ RF energy, applied between the snare loop and a grounding pad, to provide a cutting arc. The cutting arc passes through the tissue as the snare loop is tightened around the polyp cauterizing the lesion and assisting the snare in excising the polyp. In a monopolar snare, the RF energy typically travels through a significant portion of the polyp from the snare to the ground.

Bipolar snares have also been developed which are formed by two electrode wires electrically insulated from each other. Alternatively, a snare loop may be formed from a first electrode wire while a second electrode wire is exposed at an end of the lumen or sheath. Thus, as the bipolar snare is tightened around the polyp and RF energy is applied across the two electrodes, the polyp is severed from the surrounding tissue.

However, these arrangements have resulted in unwanted heat being generated due to short circuiting or uneven distribution of the area of contact between the electrodes and the surface of the polyps.

SUMMARY OF THE INVENTION

The present invention is directed to a polypectomy snare for excising a polyp from an internal body cavity, comprising a cable including first and second conductors insulated from one another, wherein a portion of the cable forms a loop and wherein the first and second conductors are arranged in an alternating distribution around a periphery of the loop, the first conductor having a plurality of exposed portions forming a plurality of first electrodes and the second conductor having a plurality of exposed portions forming a plurality of second electrodes, the first and second electrodes being distributed around the periphery of the loop.

The present invention is further directed to a method of excising a polyp comprising the steps of placing a snare around the polyp, wherein the snare includes a plurality of electrodes alternating in polarity around a tissue contacting surface thereof, reducing a diameter of the snare to bring the tissue contacting surface of the snare into contact with the polyp and applying electrical energy to the electrodes so that an electrical current flows between the electrodes, through tissue of the polyp.

These and other characteristics, and advantages of the present invention will become apparent in view of the description and accompanying drawings that follow.

BRIEF DESCRIPTION OF THE DRAWINGS

FIG. 1 shows a top view of an embodiment of the present invention;

FIG. 2 shows a side view of a distal end of the device of FIG. 1, including the snare loop;

FIG. 3 shows a side view of section A—A of the snare loop of FIG. 1;

FIG. 4 shows a second embodiment of the snare loop section of the present invention;

FIG. 5 shows a cross-sectional view of the embodiment of FIG. 4 through section A—A;

FIG. 6 shows a partial view of the snare loop wire according to the second embodiment of the invention;

FIG. 7a shows a cross-sectional view of an alternative embodiment of the snare loop cable of the present invention;

FIG. 7b shows a cross-sectional view of the snare loop cable of FIG. 7a at a different location along the snare loop cable;

FIG. 8a shows another embodiment of the conductors according to the present invention;

FIG. 8b shows yet another embodiment of the conductors according to the present invention;

DETAILED DESCRIPTION

Figure 9:
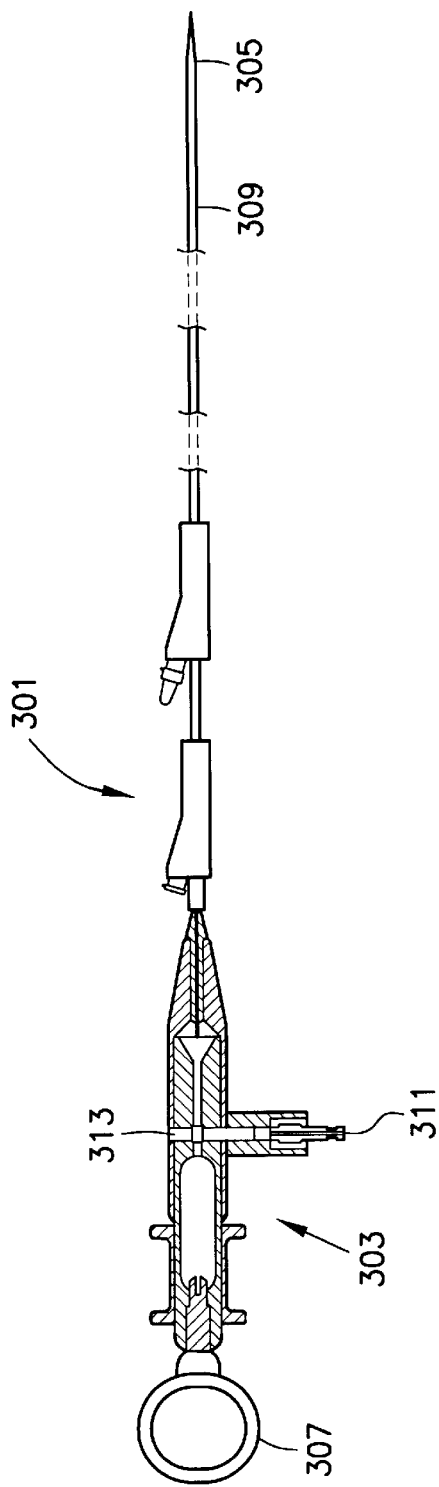
FIG. 9 shows a partially cross-sectional side view of a bipolar electrosurgical needle knife.

FIG. 1 shows an embodiment of a bipolar polypectomy snare 1 according to the present invention. The snare 1 includes two wires 11, 12, disposed in a sheath 61, wherein the wires 11, 12 may be, for example, insulated stainless steel wires. Electrical connectors 73, 74 connect the wires 11, 12, respectively, to a finger handle 72 at a proximal end 2 of the snare 1. The electrical connectors 73, 74 also provide connectors by which a source of RF energy (not shown) may be supplied to the snare 1. The finger handle 72 is slidably mounted in a handle housing 71 including a distal stop 81, disposed at the junction of the handle housing 71 and the sheath 61. The distal stop 81 defines a distal most position of the finger handle 72. The handle housing 71 includes, at its proximal end, a thumb handle stop 75. The thumb handle stop 75 provides, for example, both a convenient gripping mechanism for a user to hold the snare 1 as well as a proximal delimitation for the sliding range of the finger handle 72.

A snare loop 5 is formed at the distal end 3 of the snare 1. The wires 11, 12 extend distally from the sheath 61 and are twisted or wrapped together about one another in a helical manner to form a dual strand braid. The end 4 of the dual strand braid is turned back and crimped to wires 11, 12 to form the snare loop 5. A crimp 50 may be used to hold the end 4 of the dual strand braid to a body portion of the wires 11, 12. In the embodiment shown in FIG. 1, for example, substantially the entire length of the snare loop 5 is constructed from the helically wound dual strand braid of wires 11, 12. As shown in FIG. 2, the end 4 of the dual strand braid may be crimped back to a body portion of the wires 11, 12 in an offset position. As discussed more fully below, the offset may advantageously prevent a short circuit in the snare loop 5 when the snare loop 5 is retracted into the sheath 61.

FIG. 3 shows the snare loop 5 through section A—A of FIG. 1. The insulated wires 11, 12 are substantially parallel at region 50.1, which corresponds approximately to the location of the crimp 50. Proceeding distally from region 50.1, the wires 11, 12 are twisted together to form a substantially helical or spiral configuration. The spiral configuration arranges sections of the wires 11, 12 along an outer surface of the snare loop 5 in an alternating sequence. Thus, section 11.1 of wire 11 is adjacent to section 12.1 of wire 12. As the wires 11, 12 are substantially insulated there is no electrical contact directly between them. However, on the surface of each spiral facing the inside of the snare loop 5, portions of the wires 11, 12 are exposed to form exposed electrodes thereon. For example, exposed electrodes 21e and 21f represent two of the many exposed electrodes of wire 11. The exposed electrodes 21e, 21f alternate respectively with exposed electrodes 22e and 22f of wire 12. In this manner, exposed electrodes of wire 11 alternate with exposed electrodes of wire 12 around the inner periphery of the snare loop 5.

In operation, the snare 1 is inserted into a body cavity (not shown) so that the snare loop 5 is in the vicinity of a polyp. The snare loop 5 is manipulated in size by extending or retracting the snare loop 5 relative to the sheath 61. The snare loop 5 may be enlarged, for example, by moving the finger handle 72 distally such that the effective diameter of the snare loop 5, that is, the portion of the snare loop 5 external to the sheath 61, increases. When the snare loop 5 has been positioned around the polyp, the finger handle 72 may be moved proximally, to thereby constrict the snare loop 5 around the polyp.

When the snare loop 5 is retracted into the sheath 61, the exposed electrodes (e.g. 21e, 22e, 21f, 22f) do not come into direct contact with opposing exposed electrodes on the opposite side of the snare loop because of the offset in crimp thereby avoiding a short which could render the snare 1 inoperable. That is the end 4 of the dual strand braid is crimped offset from an axis of the wires 11,12 within the sheath 61. Thus, when the loop 5 collapses as it is drawn in to the sheath 61, opposite sides of the loop are displaced from one another in a direction substantially perpendicular to the axis and do not contact one another.

Retracting the snare loop 5 into the sheath 61 constricts the snare loop 5 around the polyp. The proximity of the polyp to the snare loop 5 allows the tissue of the polyp to complete the circuit between alternating electrodes, for example, between electrode 21b and the two adjacent electrodes, 22b, 22c. The RF power source generates a current flow through the tissue at the periphery of the polyp between adjacent electrodes excising and cauterizing the tissue. The combination of small arcs around the inner periphery of the snare loop 5 between adjacent electrodes forms a continuous cutting arc. That is, each individual arc is formed between an electrodes (e.g. 21f) and an adjacent electrode of opposite polarity (e.g. 22f).

Beneficially, according to the present invention, the circuit has a shorter path through the tissue of the polyp.

Thus, satisfactory results may be obtained with reduced power and current may be maintained at relatively a low level. When the tissue joining two adjacent electrodes on the periphery of the snare loop 5 has been cauterized, the circuit is thus opened and the current will no longer flow between those two electrodes until the snare loop 5 is constricted around the remaining polyp tissue. Thus, the current is self limiting, in that, when the tissue is cauterized, the circuit is broken and the current drops off.

FIG. 4 shows a snare loop 105 according to an alternative embodiment of the present invention. The snare loop 105 is made of a cable 101 that contains two or more conductors. The conductors are insulated from one another, but are exposed at specified points on the circumference of the cable 101. Suitable materials for the conductors include, without limitation, stainless steel, gold, silver, copper, aluminum, titanium, and other electrically conducting materials. The insulating materials may be chosen considering the need for some degree of flexibility and temperature resistance. The insulating materials include, without limitation, polytetraflouroethylene (PTFE or Teflon™ and Kapton™.

Preferably, the cable 101 may be pre-formed into a loop, such as is shown in FIG. 4. The cable 101 should have sufficient elastic memory such that, after being deformed under external forces, it will substantially return to its original shape when the external forces are removed.

FIG. 5 shows the cross section of the cable 101 of Fig. The cable 101 includes a centrally located set of core wires 102 which is surrounded by an insulation layer 103. The core wires 102 may be either metallic or polymeric and may be single or multiple stranded, eg. Teflon™, Kevlar™ or other composite materials. On the exterior of the cable 101 are alternating regions of insulation 104, positive pole over wires 105, insulation 106 and negative pole overwires 107. The alternating regions 104, 105, 106, 107 may be, for example, wrapped spirally around the exterior of the cable 101. An alternative construction of cable 101 provides that the positive pole overwires 105 and negative pole overwires 107 are at least partially embedded into the insulation layer 103 with at least a portion of the overwires 105, 107 being exposed from the surface of the insulation layer 103.

FIG. 6 shows an exploded view of the cable 101 through section B—B of FIG. 4. As can be seen, the positive and negative pole overwires 105, 107 alternate with the regions of insulation 104, 106. Preferably, the positive and negative pole overwires 105, 107 alternate with each other across each insulation region 104, 106 so that the poles of the RF energy are always opposed to one another across the insulation region 104, 106. The snare wire comprises at least 2 strands of wire 105, 107. One strand for each pole of the RF energy. The number of strands of wire may be increased by a progression of 2, 4, 8, 12, and upwards by multiples of 4. For example, as shown in FIG. 6, 2 strands are used to form the cable 101.

The pitch or lay of the overwires 105 and 107 may vary depending on the performance characteristics required. For example, the spacing 108 between the overwires 105 and 107 may be designed so that the RF energy does not arc across the spacing 108 to create a short. Additionally, the spacing 108 should be close enough that the RF energy can overcome the impedance of the tissue of the polyp that lies between the overwires 105 and 107 such that a current flows through the polyp to the required burn depth.

The diameter d of the cable 101 may be varied depending on the particular application. For example, a diameter d of approximately 0.01 inches or smaller may be desired for some applications. Larger diameters may be desired for other applications. Additionally, the cross-section of the cable 101 does not have to be circular. The cross-section may, for example, have a shape narrower on one side than on the other as shown in FIG. 7a. Such a shape can facilitate the cutting action of the cable through the tissue of the polyp. It is noted that the distribution of the overwires 105 and 107 and insulation regions 104 and 106 about the circumference of the cable 101 may vary at different cross-sections of cable 101, providing, for example, a distribution as shown in FIG. 7b.

FIG. 8a shows another embodiment of the snare wire according to the present invention. The snare wire comprises at least 2 strands of wire 201, 202 each insulated from the other by insulation layers 203. One strand for each pole of the RF energy. The number of strands of wire may be increased by a progression of 2, 4, 8, 12, and upwards by multiples of 4. For example, as shown in FIG. 8b, 4 strands are used to form the cable 101. Strands 201 and 201.1 forming the positive pole and strands 202 and 202.1 forming the negative pole. The number of wires used for the cross section of the cable provides that wires of opposite poles are adjacent to one another. It is desired to have wires of the opposite polarity adjacent to one another to form a cutting arc of RF energy.

Figure 10:
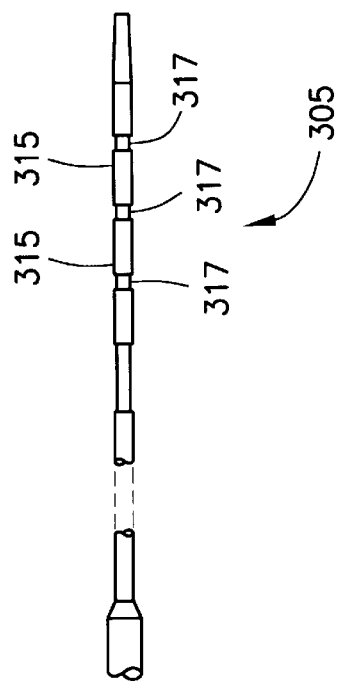
FIG. 10 shows an expanded view of the cutting portion of the bipolar needle knife of FIG. 9.

FIGS. 9 and 10 show an additional application of the present invention wherein the bipolar cable is formed as a linear needle knife and not as a snare. Namely, these figures show an electrosurgical bipolar needle knife 301 extending from a handle 303 to a distal cutting blade 305. The handle 303 includes a thumb ring 307 slidably mounted for motion relative to the handle 301 between a retracted position in which the thumb ring is spaced from a proximal end of the handle 301 and an extended position spaced from the proximal end of the handle 301. The thumb ring 307 is coupled to the cutting blade 305 so that, when the thumb ring 307 is in the extended position, the cutting blade 305 is withdrawn into a surrounding sheath 309 and, when the thumb ring 307 is in the retracted position, the cutting blade 305 is extends distally from a distal end of the sheath 309. The handle 301 also includes ports 311, 313 for coupling the positive and negative poles 315, 317, respectively, of the cutting blade 305 to a source of RF energy.

In use, the distal portion of the device 301 would be introduced to a desired location within the body and a portion of tissue to be excised would be drawn away from the surrounding tissue as described in regard to the previous embodiments. The cutting blade 305 would then be extended out of the sheath 309 by moving the thumb ring 307 from the extended position to the retracted position and the cutting blade 305 would be placed in contact with the tissue to be excised. RF energy would then be supplied to the cutting blade 305 and the blade 305 would be drawn through the tissue to excise the lesion.

While the present invention is capable of various modifications and alternate constructions, it is not intended to limit the invention to the specific embodiments disclosed herein. Rather, it is intended to cover all modifications and alternative constructions falling within the spirit and scope of the invention as expressed in the claims.

What is claimed is:

1. An apparatus for cutting tissue from a living body comprising:
   first and second conductors arranged in an alternating distribution and abutting one another, wherein at least a portion of the first conductor has a first insulative coating thereon so that the first insulative coating insulates the first and second conductors from one another, the first conductor further including a plurality of first exposed portions from which the first insulative coating has been removed, the first exposed portions forming a plurality of first electrodes and wherein the second conductor forms a plurality of second electrodes, the first and second electrodes forming a cutting edge of a cutting member.

2. The apparatus according to claim 1, wherein the first conductor and the second conductor wrap spirally about each other to form the alternating distribution along the cutting member.

3. The apparatus according to claim 1, wherein the second conductor has a second insulative coating thereon so that, with the first and second conductors abutting one another, the first and second insulative coatings are in contact with one another, and wherein the second electrodes are formed at second exposed portions of the second conductor from which the second insulative coating has been removed.

4. An apparatus for cutting tissue from a living body comprising:
   a cutting member formed of first and second conductors insulated from one another, wherein portions of the first and second conductors forming the cutting member are wound about one another in an alternating distribution and wherein the first conductor has a plurality of exposed portions forming a plurality of first electrodes and the second conductor has a plurality of exposed portions forming a plurality of second electrodes, the first and second electrodes being distributed alone a cutting edge of the cutting member, wherein the cutting member is formed as a loop formed by connecting distal ends of the wound first and second conductors to proximal portions thereof using an offset crimp, wherein the distal ends of the wound first and second conductors are offset from the proximal portions in a direction perpendicular to a longitudinal axis of the proximal portions.

5. The apparatus according to claim 4, further comprising a sheath into which the loop may be withdrawn and from which the loop may be extended.

6. The apparatus according to claim 5, wherein the loop is movable relative to the sheath such that an effective diameter of the loop may be altered by changing the position of the loop relative to the sheath.

7. The apparatus according to claim 4, wherein a cross-sectional area of a cable formed by the wound first and second conductors is narrower in a region facing an inside of the loop.

8. An apparatus for cutting tissue from a living body comprising:
   a cutting member formed of first and second conductors insulated from one another, wherein portions of the first and second conductors forming the cutting member are wound about one another in an alternating distribution and wherein the first conductor has a plurality of exposed portions forming a plurality of first electrodes and the second conductor has a plurality of exposed portions forming a plurality of second electrodes, the first and second electrodes being distributed along a cutting edge of the cutting member, wherein the first and second conductors are wrapped spirally around a plurality of insulated core wires.

9. The apparatus according to claim 8, wherein the first and second conductors are partially embedded in an outer insulation layer of the insulated core wires.

10. An apparatus for excising tissue from a living body, comprising:
    a cable extending from a proximal end which, when in an operative position, extends out of the living body, to a distal end which, when in the operative position, is located within the living body proximate to the tissue to be excised, the cable including first and second conductors abutting one another and arranged in an alternating distribution along a cutting edge of the apparatus, wherein the first conductor includes an insulative coating thereon insulating the first conductor from the second conductor and a plurality of exposed portions from which the insulative coating is removed forming a plurality of first electrodes and wherein the second conductor includes a plurality of second electrodes, the first and second electrodes being distributed in alternating distribution along a periphery of the cutting edge.

11. An apparatus according to claim 10, wherein a distal portion of the cable is formed as a loop with the cutting edge being formed on an interior surface of the loop.

12. An apparatus according to claim 11, further comprising:
  a sheath into which the loop is drawn when in a retracted configuration, wherein in an extended configuration, the loop extends from a distal end of the sheath; and
  a handle coupled to the proximal end of the cable and to the sheath so that movement of the handle relative to the sheath moves the loop between the extended and retracted configurations.

13. A method of cutting tissue including the steps of:
  positioning a tissue cutting device adjacent to a portion of tissue to be cut, wherein the tissue cutting device includes first and second conductors wound about one another in an alternating distribution, wherein a portion of the first conductor includes an insulative coating insulating the first and second conductors from one another, portions of the first conductor being uninsulated to form a plurality of first electrodes, and the second conductor forming a plurality of second electrodes, the first and second electrodes being distributed in an alternating distribution along a tissue contacting surface of the tissue cutting device;
  bringing the tissue contacting surface of the tissue cutting device into contact with the tissue to be cut; and
  applying electrical energy to the first and second electrodes so that an electrical current flows between the first and second electrodes, through the tissue to be cut.

* * * * *